United States Patent
Esmail et al.

(10) Patent No.: US 9,821,312 B2
(45) Date of Patent: Nov. 21, 2017

(54) INTEGRATED MICROFLUIDIC SYSTEM, METHOD AND KIT FOR PERFORMING ASSAYS

(71) Applicant: Bio-Rad Laboratories, Inc., Hercules, CA (US)

(72) Inventors: Adnan Esmail, Boston, MA (US); John Healy, Acton, MA (US); Tony Hung, Cambridge, MA (US); Sepehr Kiani, Watertown, MA (US); Pascaline Mary, Cambridge, MA (US); Tal Raz, Brookline, MA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 14/427,404

(22) PCT Filed: Sep. 12, 2013

(86) PCT No.: PCT/US2013/059517
§ 371 (c)(1),
(2) Date: Mar. 11, 2015

(87) PCT Pub. No.: WO2014/043388
PCT Pub. Date: Mar. 20, 2014

(65) Prior Publication Data
US 2015/0209785 A1 Jul. 30, 2015

Related U.S. Application Data

(60) Provisional application No. 61/700,099, filed on Sep. 12, 2012.

(51) Int. Cl.
*B01L 3/00* (2006.01)
*G01N 35/08* (2006.01)
*B01L 7/00* (2006.01)

(52) U.S. Cl.
CPC ......... *B01L 3/502784* (2013.01); *B01L 7/525* (2013.01); *G01N 35/08* (2013.01);
(Continued)

(58) Field of Classification Search
CPC .......................... B01L 3/502784; G01N 35/08
See application file for complete search history.

(56) References Cited

U.S. PATENT DOCUMENTS

| 8,528,589 B2 | 9/2013 | Miller et al. |
| 8,535,889 B2 | 9/2013 | Larson et al. |

(Continued)

FOREIGN PATENT DOCUMENTS

| CN | 102205227 | 10/2011 |
| EP | 2364774 A2 | 9/2011 |

(Continued)

OTHER PUBLICATIONS

International Search Report and Written Opinion from PCT/US2013/059512, dated Dec. 2, 2013.
(Continued)

*Primary Examiner* — Melanie Y Brown
(74) *Attorney, Agent, or Firm* — Kilpatrick Townsend and Stockton, LLP

(57) ABSTRACT

The present invention provides a microfluidic system, method and kit for performing assays. The system may comprise a microfluidic device and a detector, wherein the assay yields results that may be read by a detector and analyzed by the system. The assay may comprise one or more chemical or biological reaction against, or performed on, a sample or multiple samples. The sample(s) may become larger and/or smaller during the performance of the assay. The sample(s) may be present within a vehicle, or on a carrier within a vehicle, in the microfluidic device, and wherein the vehicle may become larger and/or smaller
(Continued)

during the performance of the assay. The assay may be a cascading assay comprising a series of multiple assays, wherein each assay may be the same or different, and wherein each assay in the series of multiple assays may further comprise one or more process or step.

21 Claims, 5 Drawing Sheets

(52) U.S. Cl.
CPC .......... *B01L 7/52* (2013.01); *B01L 2200/0673* (2013.01); *B01L 2200/14* (2013.01); *B01L 2200/16* (2013.01); *B01L 2300/0636* (2013.01); *B01L 2300/0816* (2013.01); *B01L 2300/0864* (2013.01); *B01L 2300/0867* (2013.01); *B01L 2300/0883* (2013.01); *B01L 2300/18* (2013.01); *B01L 2300/1861* (2013.01); *B01L 2400/0415* (2013.01); *B01L 2400/0433* (2013.01); *B01L 2400/0448* (2013.01); *B01L 2400/088* (2013.01); *Y10T 436/143333* (2015.01); *Y10T 436/2575* (2015.01)

(56) References Cited

U.S. PATENT DOCUMENTS

| | | |
|---|---|---|
| 2004/0089548 A1 | 5/2004 | Mehta et al. |
| 2006/0078888 A1 | 4/2006 | Griffiths et al. |
| 2008/0014589 A1 | 1/2008 | Link et al. |
| 2009/0068170 A1* | 3/2009 | Weitz .................. G01N 33/505 424/130.1 |
| 2010/0015606 A1* | 1/2010 | Davies ................ B01F 13/0071 435/287.2 |
| 2011/0053151 A1 | 3/2011 | Hansen et al. |
| 2011/0053798 A1* | 3/2011 | Hindson .............. C12Q 1/6844 506/12 |
| 2011/0151578 A1 | 6/2011 | Abate et al. |
| 2011/0218123 A1 | 9/2011 | Weitz et al. |
| 2011/0250597 A1 | 10/2011 | Larson et al. |
| 2011/0267457 A1 | 11/2011 | Weitz et al. |
| 2012/0015822 A1 | 1/2012 | Weitz et al. |
| 2012/0080544 A1 | 4/2012 | Shinoda |
| 2012/0108721 A1* | 5/2012 | Mazutis ................ B01F 3/0807 524/236 |
| 2012/0132288 A1 | 5/2012 | Weitz et al. |
| 2012/0219947 A1 | 8/2012 | Yurkovetskty et al. |
| 2012/0220494 A1 | 8/2012 | Samuels et al. |
| 2012/0222748 A1 | 9/2012 | Weitz et al. |
| 2012/0309002 A1 | 12/2012 | Link |
| 2014/0354795 A1 | 12/2014 | Tracy et al. |
| 2015/0024945 A1 | 1/2015 | Healy |

FOREIGN PATENT DOCUMENTS

| | | | |
|---|---|---|---|
| EP | 2662135 A2 | | 11/2013 |
| WO | 2007/081385 A2 | | 7/2007 |
| WO | 2007/081387 A1 | | 7/2007 |
| WO | WO2010/080134 | * | 7/2010 |
| WO | 2012/078710 A1 | | 6/2012 |
| WO | 2012/135201 A1 | | 10/2012 |
| WO | 2012/135259 A1 | | 10/2012 |
| WO | 2012/135327 A1 | | 10/2012 |
| WO | 2013/095737 A2 | | 6/2013 |
| WO | 2013/122826 A1 | | 8/2013 |
| WO | 2013/165748 A1 | | 11/2013 |
| WO | 2014/093976 A1 | | 6/2014 |
| WO | 2014/117088 A1 | | 7/2014 |
| WO | 2014/176599 A1 | | 10/2014 |

OTHER PUBLICATIONS

U.S. Appl. No. 14/470,860, filed Aug. 27, 2014.
U.S. Appl. No. 14/502,948, filed Sep. 30, 2014.
Extended European Search Report dated Sep. 9, 2016 in European Patent Application No. 138372289, all pages.

* cited by examiner

INTEGRATED MICROFLUIDIC SYSTEM, METHOD AND KIT FOR PERFORMING ASSAYS

CROSS-REFERENCES TO RELATED APPLICATIONS

The present application is a US national phase of PCT/US2013/059517, filed Sep. 12, 2013, which claims priority to U.S. Provisional Patent Application Ser. No. 61/700,099, filed Sep. 12, 2012, each of which are incorporated by reference for all purposes.

The foregoing application, and all documents cited therein or during its prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention is in the technical fields of microfluidics, and those of the biological and chemical sciences, including biochemistry, genetics, cell biology and molecular biology. More particularly, the present invention relates to a microfluidic system, method and kit for performing assays.

BACKGROUND OF THE INVENTION

In most biological and chemical laboratories, e.g., molecular biology, genetics and biochemistry laboratories, tests or processes (referred to as "assays") are handled in discrete process steps. Each step is manually or robotically transferred between or among processing elements. For example, in nucleic acid assays, PCR amplification of the target of interest is often performed before additional assay steps take place such as hybridization or fluorescent labeling. In another example, as is the case in proteomic assays, the sample may be allowed to interact with one reagent as a first step, and then with another reagent in a second step to generate the readable output. Each of these manual or robotic steps introduces processing delays and the risk for errors. Accordingly, there is a need for a system for performing assays efficiently and reliably.

The present invention provides a system, method and kit for performing efficient and reliable biological and chemical assays.

Citation or identification of any document in this application is not an admission that such document is available as prior art to the present invention.

SUMMARY OF THE INVENTION

The present invention generally pertains to a system for performing assays. More specifically, the present invention pertains to a microfluidic device for performing biological and chemical assays. In one embodiment, the system may comprise a microfluidic device and a detector. In one aspect of this embodiment, the assay yields results that may be read by a detector and analyzed by the system. In another aspect of this embodiment, the assay may be selected from a biological or chemical assay. In yet another aspect of this embodiment, the assay may comprise one or more reaction against, or performed on, a sample. In one embodiment, the sample may become larger during the performance of the assay. In another embodiment, the sample may become smaller during the performance of the assay.

In yet another embodiment, the sample may be present within a vehicle in a microfluidic device. In one aspect of this embodiment the vehicle may become larger during the performance of the assay. In another aspect of this embodiment, the vehicle may become smaller during the performance of the assay. In still another embodiment, a sample may be on the surface of a carrier. In one aspect of this embodiment, the sample may be on the surface of a carrier within a vehicle in a microfluidic device.

In another embodiment, the assay is performed on multiple samples. In yet another embodiment, the assay is a cascading assay. In one aspect of this embodiment, the cascading assay comprises a series of multiple assays, wherein each assay may be the same or different, and wherein each assay in the series of multiple assays may further comprise one or more process or step.

The present invention also pertains to methods for performing assays comprising the system described previously and further herein. The present invention further pertains to a kit comprising the system and reagents necessary for performing the methods according to the present invention, as described previously and further herein.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example but not intended to limit the invention solely to the specific embodiments described, may best be understood in conjunction with the accompanying drawings.

DETAILED DESCRIPTION OF THE INVENTION

Figure 1:
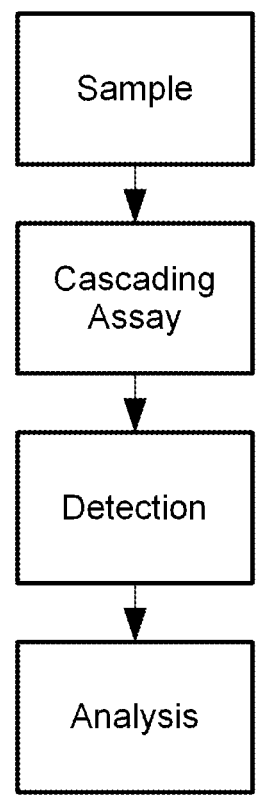
FIG. 1 is a block diagram illustrating the general features of the system, according to the present invention.

The present invention generally pertains to a system for performing biological and chemical assays, referred to individually and collectively as "assays" and include but are not limited to, any test or process that may be performed in a biological or chemical laboratory (e.g., molecular biology, genetics and biochemistry laboratories). More specifically, an assay may be any biological or chemical reaction against, or performed on, a sample, the results of which may be read by a detector and analyzed by the system according to the present invention.

A "sample(s)", "one or more samples", or "sample(s) of interest" are terms used interchangeably in singular or plural form and are not intended to be limited to any particular quantity and, as used herein, may be any molecule or substance that the user wishes to gather information from. A sample may become larger or smaller (e.g., by way of inflation or partitioning, respectively) in size, volume or content during the performance of an assay. Accordingly, a sample may be amplified and/or subdivided one or more times during the performance of an assay.

In one embodiment of the present invention, a sample is present within a vehicle in a microfluidic device. In one aspect of this embodiment, multiple samples (i.e., more than one) may be present together in the same vehicle and/or may be separated into individual samples within individual vehicles at any point during an assay(s). Additionally, a vehicle comprising one or more samples may become larger or smaller (e.g., by way of inflation or partitioning, respectively) in size, volume or content during the performance of an assay. A vehicle may be amplified and/or subdivided one or more times during the performance of an assay. The system according to the present invention may further perform a "cascading assay", which is a series of multiple (i.e., more than one) assays, wherein each assay may be the same or different, and wherein each assay in the series may further comprise one or more process or step. In one aspect of this embodiment, the sample is present on a carrier within a vehicle in a microfluidic device.

"Inflation", as used herein, refers to increasing the volume or content of a vehicle by injecting or other means of transferring fluid or other components into the vehicle such as by diffusion or osmotic controlled diffusion or, in the case of a sample, refers to increasing the volume or content of a sample by amplification (e.g., PCR, cell division or other mechanism for increasing the content or volume of a sample) such that the size, volume and/or content of the sample or vehicle becomes relatively larger than prior to inflation. "Partitioning", as used herein, refers to the dividing, subdividing and/or portioning of a sample or vehicle such that the size, volume and/or content of the sample or vehicle become relatively smaller than prior to partitioning.

Accordingly, in one example, a sample within a vehicle may be amplified (e.g., by PCR, cell division or other mechanism for increasing the content of a sample) one, two or multiple times comprising multiple samples and/or partitioned one, two or multiple times into multiple individual samples within a cascading assay. Likewise, in another example, a vehicle containing a sample may be inflated one, two or multiple times and/or partitioned one, two or multiple times into multiple vehicles, wherein each vehicle may comprise one or more samples, within a cascading assay. Moreover, in yet another example, a sample present in a first vehicle may be injected into a second vehicle, wherein the second vehicle may or may not comprise one or more additional samples, within a cascading assay. Additionally, in still another example, a sample may be amplified on the surface of a carrier (e.g., a bead). In this example, the carrier may further be present within a vehicle comprising multiple carriers, wherein each carrier comprises at least one sample on its surface, and wherein each sample is subsequently separated from its respective carrier followed by selective partitioning of one or more samples from one or more other samples as the vehicle is partitioned one or more times, within a cascading assay. In this example, after a sample is separated from its respective carrier, the carrier may or may not be removed from the vehicle as the vehicle is partitioned one or more times.

FIG. 1 is a block diagram illustrating the general features of the system according to the present invention. As generally illustrated, samples enter the system and are processed through a cascading assay. At the end of the assay is a detection system, which generates a signal based on the content and results of the assay. Finally, the system analyzes those signals to determine the results of the assay. The system of the present invention further provides for detection and sorting of sample, vehicle and/or results at any and all stages of a cascading assay, according to the preference of the user, such that only relevant, selected or preferred information may be allowed to filter through in the form of a readout, thus improving throughput of a cascading assay.

The system of the present invention allows a sample of any type (introduced by the user) to be partitioned by injecting parts, portions or components of the sample into a vehicle of any type. For example, the system according to the present invention provides for injection of one sample into a multitude of vehicles, e.g., droplets, and this process may be repeated in a cascading manner wherein injected droplets may again be injected into other droplets for additional partitioning and/or introduction of new chemical reagents into a multitude of droplets. Conversely, the system of the present invention allows a multitude of droplets to be injected into a single droplet (sample joining). Sample joining preferably occurs at a junction between or among microfluidic channels. The direction of injection, i.e., into or out of a particular droplet by way of partitioning or by sample joining, is governed by the relative pressure in the intersecting microfluidic channels.

Figure 2:
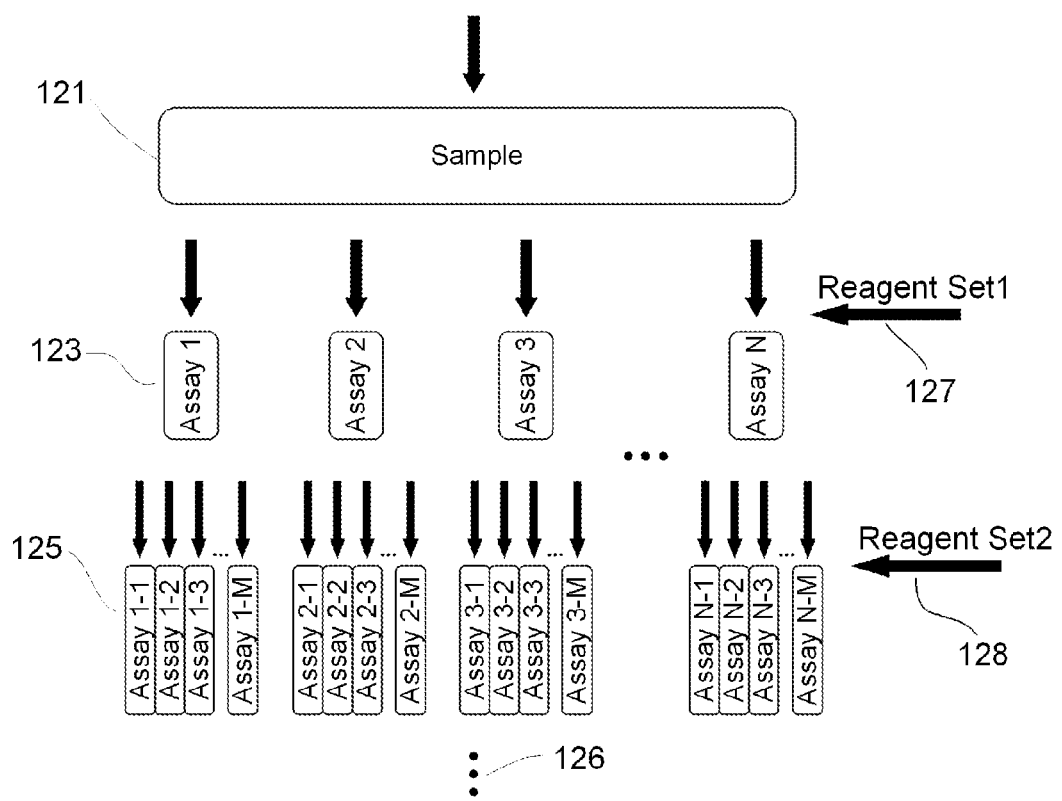
FIG. 2 is a block diagram illustrating the general features of a cascading assay as may be performed by the system, according to the present invention.

FIG. 2 is a block diagram illustrating the general features of a cascading assay as may be performed by the system according to the present invention. In the system 120 illustrated in FIG. 2, a sample 121 is injected into the system 120 by the user. The sample 121 is then partitioned into multiple "N" segments 123, into which any necessary assay reagents are added by injection or inflation (as illustrated, for example, by Reagent Set 1 127) and upon which one or more assays may be performed. By way of example, the first three N segments 123 are referred to as "Assay 1" for the assay performed on partitioned N segment 1, "Assay 2" for the assay performed on partitioned N segment 2 and "Assay 3" for the assay performed on partitioned N segment 3, respectively and so forth, all the way through "Assay N" for the assay performed on the last partitioned N segment for each N segment illustrated in FIG. 2.

Next, each of the N segments 123 previously assayed is further partitioned into multiple "M" segments 125, into which any necessary assay reagents are added by injection or inflation (as illustrated, for example, by Reagent Set 2 128) and upon which further assays may be performed. By way of example, each assay performed on each M segment partitioned from N segment 1 is referred to as "Assay 1-1", "Assay 1-2" and "Assay 1-3", respectively and so forth all the way through "Assay 1-M" for the last assay performed on an M segment partitioned from N segment 1 illustrated in FIG. 2. Likewise, each assay performed on each M segment partitioned from N segment 2 is referred to as "Assay 2-1", "Assay 2-2" and "Assay 2-3", respectively and so forth all the way through "Assay 2-M" for the last assay performed on an M segment partitioned from N segment 2. Moreover, each assay performed on an M segment partitioned from N segment 3 is referred to as "Assay 3-1", "Assay 3-2" and "Assay 3-3", respectively and so forth all the way through "Assay 2-M" for the last assay performed on an M segment partitioned from N segment 3 illustrated in FIG. 2. Each of the N segments 123 may be partitioned multiple times resulting in any multitude of M segments 125, each of which may be assayed any multitude of times, as illustrated by "Assay N-1", "Assay N-2", "Assay N-3" all the way through "Assay N-M" as illustrated in FIG. 2. These processes of this cascading assay may be repeated any number of times by the system of the present invention, as indicated by 126 in FIG. 2.

In one embodiment of the present invention, the system is an integrated microfluidic device. A "microfluidic device", as used herein, is a device that enables a means of effecting a deterministic function on liquid or gas fluids at small scales typically measured in volumes such as, for example, milliliter (mL), microliter (µL), nanoliter (nL), picoliter (pL), or femtoliter (fL) volumes and/or by physical scale such as millimeter (mm), micrometer (µm) (also referred to as "micron"), nanometer (nm), and so forth. Functions may include mixing, splitting, sorting, heating, and so forth. Microfluidic devices may comprise microfluidic channels as a means for transferring fluids or samples from one point to another and are typically of uniform cross section in the mm, µm or nm scale.

A wide variety of methods and materials exists and will be known and appreciated by one of skill in the art for construction of microfluidic channels and networks thereof, such as those described, for example, in U.S. Pat. No. 8,047,829 and U.S. Patent Application Publication No. 20080014589, each of which is incorporated herein by reference in its entirety. For example, the microfluidic channel may be constructed using simple tubing, but may further involve sealing the surface of one slab comprising open channels to a second flat slab. Materials into which microfluidic channels may be formed include silicon, glass, silicones such as polydimethylsiloxane (PDMS), and plastics such as poly(methyl-methacrylate) (known as PMMA or "acrylic"), cyclic olefin polymer (COP), and cyclic olefin copolymer (COC). The same materials can also be used for the second sealing slab. Compatible combinations of materials for the two slabs depend on the method employed to seal them together. The microfluidic channel may be encased as necessary in an optically clear material to allow for optical excitation (resulting in, e.g., fluorescence) or illumination (resulting in, e.g., selective absorption) of a sample as necessary, and to allow for optical detection of spectroscopic properties of light from a sample, as the sample is flowing through the microfluidic channel. Preferred examples of such optically clear materials that exhibit high optical clarity and low autofluorescence include, but are not limited to, borosilicate glass (e.g., SCHOTT BOROFLOAT® glass (Schott North America, Elmsford N.Y.)) and cyclo-olefin polymers (COP) (e.g., ZEONOR® (Zeon Chemicals LP, Louisville Ky.)).

In one embodiment of the present invention, the sample may comprise one or more of the following, in either singular or plural form and in any combination within a cascading assay: a single-phase flow, the composition of which may vary with time; a cell or microorganism or collection of cells or microorganisms (including any eukaryotic or prokaryotic cell or microorganism, including but not limited to those selected from humans, animals, plants, fungi, bacteria, viruses, protozoa, yeasts, molds, algae, rickettsia, and prions); proteins; peptides; nucleic acid sequences, including but not limited to, any nucleic acid such as genomic DNA, mitochondrial DNA, RNA, or synthetic DNA or RNA; oligonucleotide probes; analytes; drugs; or a chemical reaction comprising one or more reagent or reaction component, including but not limited to, organic and inorganic chemicals, enzymes (including polymerase enzymes), buffers, and dNTPs.

In one embodiment of the system of the present invention, the sample is present within a vehicle and, optionally, on a carrier within a vehicle. The vehicle and/or carrier may each comprise fluids, emulsions, droplets, beads, cells, and/or microorganisms, in either singular or plural form and in any combination within a cascading assay. One or more vehicles, according to the present invention, may be used to perform various functions, including but not limited to, serving as reaction vessels for performing chemical or biological reactions; collectively encompassing a library of elements, including but not limited to a library of oligonucleotide probes; or as lenses for focusing a laser for optical applications.

In one aspect of this embodiment of the system of the present invention, the vehicle and/or carrier comprise a fluid. A "fluid", as used herein, is any aqueous or lipophilic phase capable of flowing freely. In one example, the system of the present invention may be used to perform a cascading assay on one or more samples present within a fluid, whereby the volume and/or content/components of the fluid and/or the size and/or content/components of the sample may be made larger or smaller in the process of the cascading assay, followed by separation of the fluid into individual fluids comprising individual samples, followed by detection and analysis of the samples by the system of the present invention.

In another aspect of this embodiment of the system of the present invention, the vehicle and/or carrier comprise an emulsion. An "emulsion", as used herein, is a stable mixture of at least two immiscible or partially immiscible liquids. In general, immiscible liquids tend to separate into two distinct phases. Accordingly, a surfactant may be added to stabilize the emulsion by reducing surface tension between the at least two immiscible or partially immiscible liquids and/or to stabilize the interface. For example, an emulsion may comprise a plurality of aqueous droplets in an immiscible oil, such as fluorocarbon oil, silicon oil or hydrocarbon oil (including, but not limited to, petroleum and mineral oil) where the droplet size ranges from about 0.5 to about 5000 microns in diameter.

In one aspect of this embodiment, the vehicle and/or carrier comprise a droplet. A "droplet", as used herein, means an isolated hydrophilic or hydrophobic phase within a continuous phase having any shape, for example but not limited to, cylindrical, spherical and ellipsoidal, as well as flattened, stretched or irregular shapes and so on. In one embodiment of the invention, one or more droplets are contained within an emulsion. In another embodiment of the invention, one or more droplets are contained within an emulsion in a microfluidic device. In another embodiment, the system may perform one or more assays as part of a cascading assay, wherein each assay may have one or more steps.

For example, a sample may be injected into one or more droplets within a first set of droplets in which an assay may take place, after which sample may be removed from one or more droplets of the first set of droplets and injected into one or more droplets within a second set of droplets in which an assay may take place, after which a sample may be removed from one or more droplets of the second set of droplets and injected into one or more droplets within a third set of droplets in which an assay may take place, and so forth, and wherein a sample from one or more droplets within one or more sets of droplets may be detected and analyzed by the system according to the present invention.

In another example, a first chemical reaction may take place in one or more droplets within a first set of droplets, followed by a second chemical reaction that may take place in one or more droplets within a second set of droplets, followed by a third chemical reaction that may take place in one or more droplets within a third set of droplets, and so forth, and wherein the results of each chemical reaction may be detected and analyzed by the system according to the present invention.

In another example, the system of the present invention may be used to perform a cascading assay comprising injection of multiple substantially controlled volumes into or out of one or more droplets, wherein each droplet may comprise one or more samples. In this example, the system may comprise a microfluidic channel through which droplets flow, one or more injection channels which may comprise one or more fluids and/or emulsions, and an injection inlet which may be associated with each injection channel. The microfluidic channel may intersect with the injection inlet associated with each of the one or more injection channels, such that each injection inlet, and the fluid and/or emulsion within each respective injection channel, may be connected to the microfluidic channel at a region referred to as an injection interface. In one embodiment, each injection channel may further comprise one or more subchannels, wherein each subchannel may comprise a fluid and/or emulsion, and wherein each subchannel may intersect with the microfluidic channel at the respective injection inlet associated with the injection channel comprising the particular subchannel, and wherein each subchannel may communicate with the microfluidic channel at an injection interface.

In this example, the system may further comprise a mechanism for disrupting at least a portion of the interface between a droplet flowing in a microfluidic channel and a fluid and/or emulsion in an injection channel, resulting in injection of a relatively controlled volume either into or out of a droplet and, hence, a respective increase or decrease in the volume of the droplet relative to prior to injection. An "interface", as used herein when referring to the interface between a droplet and a fluid and/or emulsion, is one or more region where two immiscible or partially immiscible phases (e.g., a droplet and a fluid or emulsion) are capable of interacting with each other. Upon disruption of the interface, there is a relative flow of volume either from the injection channel and into the droplet, or out of the droplet and into the injection channel, all via the injection inlet associated with the particular injection channel. As the droplet continues to flow past the injection inlet, there is a shearing force that breaks the contact between the droplet and the fluid and/or emulsion, followed by restoration of the interface and end of volume flow between the droplet and the fluid and/or emulsion. Accordingly, as droplets flow through the microfluidic channel, substantially controlled volumes may be either injected into or out of each droplet by way of each injection inlet associated with each of the one or more injection channels.

The direction and rate of volume may be controlled by controlling various factors of the vehicle, carrier, and/or system components, including but not limited to, a mechanism of disrupting the interface between a droplet and a fluid and/or emulsion (discussed further below); the shape, curvature and/or velocity of a carrier and/or vehicle; the pressure in the injection channel and/or the microfluidic channel relative to one another; the surface tension of the carrier and/or vehicle; the geometry of the injection inlet, and so forth, as will be known and appreciated by one of skill in the art. The above factors may, in some instances, result in forces acting on the system of the present invention, as described below.

For example, the injection inlet should be constructed such that the pressure of the system may be balanced to substantially prevent fluid and/or emulsion in the injection channel from flowing into a microfluidic channel unless there is a droplet present in the microfluidic channel and in direct contact with an injection interface, and there is sufficient activation energy to foster injection of volume between the droplet in the microfluidic channel and the fluid and/or emulsion in an injection channel. Accordingly, when there is no droplet in direct contact with an injection interface or, in instances where there is a droplet in direct contact with an injection interface but there is no mechanism for disrupting the interface between the droplet and a fluid and/or emulsion, there is substantially no net positive or net negative flow of volume into or out of the droplet or into or out of an injection channel because the forces pushing volume out of an injection channel and into the droplet are substantially balanced by the forces pushing volume out of the droplet and into the injection channel. Accordingly, the system of the present invention is constructed to substantially prevent dripping of fluid and/or emulsion from an injection channel into a microfluidic channel when there is no droplet in direct contact with an injection interface or, in instances where there is a droplet in direct contact with an injection interface but there is no mechanism for disrupting the interface between the droplet and a fluid and/or emulsion.

The mechanism for disrupting the interface between a droplet and a fluid and/or emulsion may be selected from any passive or active method, or combinations thereof, known and appreciated by one of skill in the art. Xu, et al., "Droplet Coalescence in Microfluidic Systems", *Micro and Nanosystems* (2011) vol. 3, no. 2, pp. 131-136, the entirety of which is incorporated herein by reference, describes many interface disruption mechanisms in the context of droplet coalescence but the same apply for injection of multiple substantially controlled volumes into or out of a droplet, as will be known, understood and appreciated by one of skill in the art.

Passive methods for disrupting the interface do not require external energy and rely primarily on the structure and surface properties of the microfluidic channel and associated injection channels and respective injection inlets. Passive methods for disrupting the interface include, but are not limited to, flow trapping and surface modification, which are further described by Xu, et al. and will be known and appreciated by one of skill in the art.

Examples of passive methods for disrupting the interface include, but are not limited to, the use of a localized hydrophilic region in a microfluidic channel, wherein the microfluidic channel comprises hydrophobic walls and contains aqueous-based droplets in a continuous oil phase flowing therein. The hydrophobic walls of the microfluidic channel prevent wetting of droplets and promote the presence of a thin layer of the continuous phase between the droplets and the microfluidic channel surface. However, when the microfluidic further comprises a localized region that is relatively hydrophilic, wetting of the droplets occurs as they flow pass this localized region, resulting in disruption of the previously stable interface and injection of fluid and/or emulsion either into or out of the droplet. Once the droplets flow past this localized region, the continuous phase will naturally re-wet the microfluidic channel wall and, thus, promote reformation and stabilization of the interface between the droplets and the fluid and/or emulsion. A localized hydrophilic region may be created in a hydrophobic microfluidic channel by various methods known and appreciated by one of skill in the art, including but not limited to, constructing the microfluidic channel with a material having surface chemistry that may be initiated with ultraviolet (UV) light, such that shining UV light to the localized region will induce said surface chemistry resulting in a change in the material surface property of the region from relatively hydrophobic to relatively hydrophilic.

Other examples of passive methods for disrupting the interface include creating posts or other disruptions in the path of the droplet intended to increase the shear forces on the droplet as it passes through a particular region of the microfluidic channel, or, alternatively, incorporating valves into or deformations in the walls of the microfluidic channel to physically trap a droplet to promote destabilization of at least a portion of the interface. Each of these methods results in a relatively unstable interface which, as described above, reforms and stabilizes once the droplet passes the region of disruption.

Active methods for disrupting the interface require energy generated by an external field. Active methods for disrupting the interface include, but are not limited to, electrocoalescence (i.e., by applying an electric field through the use of, e.g., one or more pairs of electrodes) and dielectrophoresies (DEP), temperature and pneumatically actuated methods, including the use of lasers and acoustic pressure methods, many of which are described by Xu, et al. and will be known and appreciated by one of skill in the art.

Examples of active methods for disrupting the interface include, but are not limited to, changing the temperature in a localized region of the system, resulting in temperature-dependent viscosity and surface tension changes affecting disruption of the interface between a droplet and a fluid and/or emulsion. For example, a laser may be focused (in the form of a "laser spot") on a region of the microfluidic channel where the droplets intersect with an injection inlet, particularly encompassing an injection interface. Such spatial variation in temperature around the laser spot will promote spatial imbalance of droplet surface tension, resulting in a thermocapillary effect on and, hence, destabilizing of, the interface. In another example, acoustic pressure waves may be used to disrupt the surface of a droplet, change the wettability of a droplet or manipulate the position of a droplet. As with methods discussed previously, each of these methods results in a relatively unstable interface which, as described above, reforms and stabilizes once the droplet passes the region of disruption.

In one or more embodiments of the present invention, the mechanism for disrupting the interface between a droplet and a fluid and/or emulsion is selected from at least one pair of electrodes. In such embodiments, the at least one pair of electrodes may be positioned substantially orthogonal to the microfluidic channel. In some aspects of one or more embodiments, the at least one pair of electrodes may be positioned substantially opposite to one or more injection channel. The at least one pair of electrodes applies an electric field to one or more injection inlet of one or more injection channel. In some examples, the at least one pair of electrodes may be positioned such that the electrodes create an electric field maximally located within one or more injection inlet or at least proximate to an injection inlet.

In embodiments wherein at least one pair of electrodes is utilized as a mechanism for disrupting the interface between a droplet and a fluid and/or emulsion as described above, the electrodes may be positioned in a variety of configurations relative to other components of the system. For example, a first electrode and a second electrode of at least one pair of electrodes may be positioned above or below the microfluidic channel. In some instances, a first electrode and a second electrode of at least one pair of electrodes may be positioned essentially on opposite sides of the microfluidic channel. In other instances, a first electrode and a second electrode of at least one pair of electrodes may be positioned essentially on opposite sides of both the microfluidic channel and one or more injection channels. In yet other instances, a first electrode and a second electrode of at least one pair of electrodes may be positioned such that a plane intersects both electrodes. In still other instances, a first electrode and a second electrode of at least one pair of electrodes may be positioned to be co-planar with the microfluidic channel and/or co-planar with one or more injection channel and/or co-planar with one or more injection inlet, such that the electrodes are positioned such that a plane intersects with each of these. In still another aspect of this embodiment, only one of the electrodes in a particular pair of electrodes needs to be localized. For example, a large ground plane may serve many individual, localized electrodes. In another example, a continuous phase fluid may serve as one of the electrodes in a pair.

The electrodes may be fabricated from any suitable material, which will be understood and appreciated by one of skill in the art. For example, the electrodes may be fabricated from materials including, but not limited to, metals, metalloids, semiconductors, graphite, conducting polymers, and liquids, including but not limited to ionic solutions, conductive suspensions, liquid metals, and so forth. The electrodes may have any shape suitable for applying an electric field, as will be understood and appreciated by one of skill in the art. For example, an electrode may have an essentially rectangular shape. In this example, the electrode may be elongated and have a tip defined as a region of the electrode closest to an intersection between the microfluidic channel and one or more injection channels. The electrode tip is constructed such that an electric field maximum is created in said intersection or substantially proximate the intersection as described previously.

In some examples where more than one pair of electrodes is employed, the electrodes may be constructed to minimize interference between one or more electrodes and one or more injection channels, for example, by minimizing the unintended exposure of a first interface to an electric field by an electrode intended to expose a second interface positioned in a different location than the first interface to an electric field. In some aspects, this may be accomplished by reducing the size of the electrode tip to allow more focused application of an electric field by the electrode tip such that one or more interfaces are not unintentionally exposed to the electric field, and/or are exposed to relatively lower electric field strengths. In other aspects, the region comprising an injection channel and respective injection inlet may be modified, e.g., by adding dimension in the form of a small bump or other modification for the purpose of localizing and strengthening the electric field in that around an injection inlet. Such aspects of the present invention may be advantageous, for example, in instances where it is desired to reduce the distance between multiple microfluidic channels, each associated with multiple injection channels and respective injection inlets as part of a microfluidic device.

In embodiments where the system of the present invention may be used to perform a cascading assay comprising injection of multiple substantially controlled volumes into or out of one or more droplets, wherein each droplet may comprise one or more samples, the volume injected into or out of each droplet may be any suitable amount, depending on the embodiment, as will be appreciated and understood by one of skill in the art. For example, the volume injected into or out of each droplet may be less than about 10 µL, less than about 1 µL, less than about 100 nL, less than about 10 nL, less than about 1 nL, less than about 100 pL, less than about 10 pL, less than about 1 pL, less than about 100 fL, less than about 10 fL, less than about 1 fL and so forth. The injection inlet in these embodiments may be of any shape, including but not limited to, circular, elliptical, triangular, rectangular and so forth. The injection inlet may have an average cross-sectional dimension of less than about 100 µm, less than about 10 µm, less than about 1 µm, less than about 100 nm, less than about 10 nm, less than about 100 µm and so forth. The injection inlet may be flush with the microfluidic channel or, alternatively, may protrude into the microfluidic channel.

In another aspect of this embodiment of the system of the present invention, the vehicle and/or carrier comprise one or more beads or a collection of beads. A "bead", as used herein, refers to a fine particle used as a substrate or matrix for reactive substances and/or identifying labels in a diagnostic application, including beads of magnetic material, silica, or polymers including, but not limited to, polystyrene. In one embodiment of the invention, one or more beads or a collection of beads are contained within an emulsion. In another embodiment of the invention, one or more beads or a collection of beads are contained within an emulsion in a microfluidic device.

In one example, the vehicle is a fluid or emulsion comprising a collection of beads (carriers) wherein each bead comprises at least one sample on its surface. In this example, the system of the present invention may be used to perform a cascading assay on each sample present on the surface of each bead in the collection of beads, followed by separation of the collection of beads into individual beads, and whereby the sample on each bead is detected and analyzed by the system of the present invention.

In another example, the carrier is one bead comprising a collection of samples present on the surface of the bead, wherein the one bead is further present within a first vehicle. In this example, the system of the present invention may be used to perform a cascading assay during which each sample present on the surface of the bead is separated from the bead, wherein each sample is then injected into a second vehicle (e.g., a droplet), and wherein the bead is discarded following removal of all samples from the surface of the bead.

In another aspect of this embodiment of the system of the present invention, the vehicle and/or carrier comprise a cell or microorganism or collection of cells or microorganisms (including any eukaryotic or prokaryotic cell or microorganism, including but not limited to those selected from humans, animals, plants, fungi, bacteria, viruses, protozoa, yeasts, molds, algae, rickettsia, and prions). In one aspect of this embodiment of the invention, one or more cell or microorganism, or a collection of cells or microorganisms is further contained within a vehicle, such as a fluid or an emulsion. In another embodiment of the invention, one or more cell or microorganism, or a collection of cells or microorganisms is contained within a vehicle in a microfluidic device.

In one example, the carrier is a single cell present within a vehicle. In this example, the system of the present invention may be used to perform a cascading assay whereby the cell is replicated one or more times, resulting in a collection of cells, followed by separation of the collection of cells into individual cells, followed by destruction or lysis of each cell to release the respective contents of each cell, and whereby the contents may be amplified (optional, such as in examples encompassing DNA or RNA sequencing) followed by detection and analysis by the system of the present invention. The contents of each cell assayed in this example may further be separated into individual components and/or may be analyzed collectively or individually from single or multiple cells.

In another example, the carrier is a single microorganism present within a vehicle. In this example, the system of the present invention may be used to perform a cascading assay whereby the microorganism is replicated one or more times, resulting in a collection of microorganisms, followed by separation of the collection of microorganisms into individual microorganisms, followed by destruction or lysis of each microorganism to release the respective contents of each microorganism, and whereby the contents may be amplified (optional, such as in examples encompassing DNA or RNA sequencing) followed by detection and analysis by the system of the present invention. The contents of each microorganism assayed in this example may further be separated into individual components and/or may be analyzed collectively or individually from single or multiple microorganisms.

In one embodiment of the invention, the system comprises one or more microfluidic devices continuous with one or more microfluidic channels in conjunction with a detector. A "detector", as used herein, may be any mechanism or device for reading the output or results of an assay. For example, the detector may be an optical detector. In another example, the detector may comprise an optical train and an image sensor.

In one embodiment of the system of the present invention, samples are present within an emulsion and flow through one or more microfluidic channels and/or one or more microfluidic devices. The samples flow by being acted upon by a source of positive or negative pressure, e.g., a pressurized or evacuated air reservoir, or a syringe pump, gravity or centripetal forces, wherein the pressure source comprises any fluid or combinations of fluids, including but not limited to any gas or combination of gases (e.g., air, nitrogen, carbon dioxide, argon, and so forth) and any liquid or combinations of liquids (e.g., water, buffer, oil, and so forth), such that the samples flow or stream through the one or more microfluidic channels one and/or more microfluidic devices and are herein referred to as "flowing sample(s)" or "streaming sample(s)". In another aspect of this embodiment, the samples may flow through one or more thermally controlled regions of the system. In any aspect, while flowing through one or more microfluidic channels and/or one or more microfluidic devices, the samples are detected and analyzed by the system.

In one embodiment of the present invention, the system detects and measures spectroscopic properties of light from a sample. The light detected and measured may comprise light scattered from a sample following illumination of a sample; emitted as chemiluminescence by a chemical process within a sample; selectively absorbed by a sample following direction of a broadband light source at a sample; or emitted as fluorescence from a sample following excitation. In this embodiment, the sample further comprises a spectroscopic substance.

In one aspect of this embodiment, the spectroscopic substance comprises one or more light-scattering molecule. A "light-scattering molecule", as used herein, means a molecule capable of propagating energy in the form of light that is scattered and comprises characteristic colors of light following illumination, for example but not limited to, by a broadband light source.

In another aspect of this embodiment, the spectroscopic substance comprises one or more chemiluminescent molecule. A "chemiluminescent molecule", as used herein, means a molecule capable of emitting light as chemiluminescence as a result of one or more chemical processes. Typical examples of chemiluminescent reactions involve the catalyzed formation of unstable organic peroxides, which emit single photons as they decay to lower-energy states. A common example of a chemiluminescent compound is luminol (CAS 521-31-3), which produces a chemiluminescent reaction in the presence of an oxidizer (for example, hydrogen peroxide catalyzed with potassium ferracyanide to form oxygen) and a hydroxide salt. Examples in the art of the diagnostic application of chemiluminescence include, but are not limited to, those in which the concentration of an enzyme, which acts as a catalyst to the chemiluminescent reaction, is to be measured, as with the use of luminol to detect hemoglobin, and those in which the chemiluminescent compound is labeled directly to a reagent, as in immunoassays employing chemiluminescent complementary binding partners. One of skill in the art will know and appreciate these and many other examples of chemiluminescent reactions in the art, including those described in, for example, K. and R. Van Dyke eds. 1990, *Luminescence Immunoassay and Molecular Applications*, Boca Raton: CRC Press.

In another aspect of this embodiment, the spectroscopic substance comprises one or more selectively absorbent molecule. A "selectively absorbent molecule", as used herein, is a molecule that absorbs certain characteristic colors or wavelengths of light while allowing other colors or wavelengths of light to pass or transmit through the molecule when a broadband light source is directed at the molecule. One of skill in the art will know and appreciate the numerous selectively absorbent molecules that may be used to comprise the selectively absorbent substance/constituent according to the present invention, including but not limited to, those commercially available from Exciton (Dayton, Ohio) and QCR Solutions, Corp. (Port St. Lucie, Fla.).

In another aspect of this embodiment, the spectroscopic substance comprises one or more fluorescent molecule. A "fluorescent molecule", as used herein, means a "fluorescent material" or "fluorescent label" or "fluorophore" or "fluorescent dye", each of which as used herein may be a fluorescent molecule, a fluorescent semiconductor nanoparticle (referred to as a "quantum dot"), or a chelated lanthanide or lanthanoid, having the ability to absorb energy from light of a specific wavelength, and then emit this energy as fluorescence having another specific wavelength characteristic for the particular molecule or quantum dot. In this manner, the fluorophore will facilitate the final assay readout indicating the presence or absence of a particular target of interest in the sample.

The particular fluorophore employed is not critical to the present invention. Fluorophores are known in the art and are described, for example, by Marras, "Selection of Fluorophore and Quencher Pairs for Fluorescent Nucleic Acid Hybridization Probes", In: V. Didenko, ed. 2006. *Fluorescent Energy Transfer Nucleic Acid Probes: Designs and Protocols* (Methods in Molecular Biology, vol. 335). New Jersey: Humana Press Inc., pp. 3-16. Examples of fluorophores that may be employed in the present invention include, but are not limited to, those described by Marras 2006 and further described herein below. One of skill in the art will appreciate the various fluorescent dyes that may serve as fluorescent molecules and that may be employed in the present invention and which are available from various commercial vendors.

Examples of fluorescent dyes that may be employed in the present invention include, but are not limited to, the following: fluorescein and derivatives thereof (e.g., fluorescein isothianate (FITC), carboxyfluorescein (FAM), tetrachlorofluorescein (TET), 2',7'-difluorofluorescein (Oregon Green® 488), Oregon Green® 514 carboxylic acid, and a fluorescein with chloro and methoxy substituents (JOE and 6-JOE)); rhodamine derivatives (e.g., tetramethyl rhodamine (TAMRA), tetramethyl rhodamine iso-thiocyanate (TRITC), tetramethylrhodamine (TMR), carboxy-X-rhodamine (ROX), Texas Red (a mixture of isomeric sulfonyl chlorides and sulforhodamine; Invitrogen™) and Texas Red-X (Texas Red succinimidyl ester, which contains an additional seven-atom aminohexanoyl spacer ("X") between the fluorophore and its reactive group; Invitrogen™), and Rhodamine X); cyanine (Cy) dyes (e.g., Cy3, Cy5 and Cy5.5) and cyanine derivatives (e.g., indocarbocyanine (Quasar® 570, Quasar® 670 and Quasar® 705), Oregon Green® isothiocyanate, and eosin isothiocyanate (EITC)); N-hydroxysuccinimidyl 1-pyrenebutyrate (PYB); N-hydroxysuccinimidyl 1-pyrenesulfonate (PYS); (5-(2'-aminoethyl)aminonaphthalene (EDANS); CAL Fluor® Gold 540, CAL Fluor® Orange 560, Fluor® Red 590, CAL Fluor® Red 610, and CAL Fluor® Red 635 (proprietary fluorophores available from Biosearch Technologies, Inc.); VIC®; HEX® (a 6-isomer phosphoramidite); and NED®.

The particular quantum dot (QD) employed is not critical to the present invention. Quantum dots are known in the art and are described, for example, by Han et al., "Quantum-dot-tagged Microbeads for Multiplexed Optical Coding of Biomolecules", *Nat Biotechnol* (July 2001) vol. 19, pp. 631-635. One of skill in the art will appreciate the various quantum dots that may serve as fluorescent labels and that can be employed in the present invention and which are available from various commercial vendors. Examples of quantum dots (QDs) that may be employed in the present invention include, but are not limited to, the following: cadmium selenide (CdSe) quantum dot nanoparticles (e.g., CdSe Quantum Dot Cores, 480-640 nm emission spectra, Sigma-Aldrich®); cadmium sulfide (CdS) quantum dot nanoparticles (e.g., CdS Quantum Dot Cores, 380-480 nm emission spectra, Sigma-Aldrich®); zinc sulfide-capped cadmium selenide (ZnS-capped CdSe) nanocrystals (e.g., CdSe/ZnS Lumidots™ and CdSe/ZnS NanoDots™, 480-640 nm emission spectra, Sigma-Aldrich®); and cadmium-free quantum dots (e.g., CFQD™, 400-650 nm emission spectra, Sigma-Aldrich®).

The particular chelated lanthanide or lanthanoid employed is not critical to the present invention. Lanthanides and lanthanoids are known in the art to comprise the fifteen metallic chemical elements with atomic numbers 57 through 71, from lanthanum (La) through lutetium (Lu). Examples of lanthanides or lanthanoids in chelated form that may be employed in the present invention include, but are not limited to, the following: lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu).

Dyes may be incorporated into a vehicle, such as a droplet, either at the time of droplet formation or after droplet formation using any injection method known and appreciated by one of skill in the art. Dyes may be incorporated during droplet formation by flowing or streaming the desired dye composition as a fluid stream into a droplet-maker design. Droplet-making designs and methods include but are not limited to those described in International Patent Publications WO 2004/002627 and WO 2006/096571, each of which is incorporated herein in its entirety.

According to the method of the present invention, the sample to be tested may be analyzed for spectroscopic intensity measurements of each spectroscopic substance, wherein the spectroscopic intensity measurement of the reference spectroscopic substance may be used to correct the spectroscopic intensity measurement of one or more sample spectroscopic substances. Depending on the application, the spectroscopic properties may comprise: light scattered from a sample to be tested following illumination of the sample to be tested; light emitted as chemiluminescence by a chemical process within the sample to be tested; light selectively absorbed by a sample to be tested following direction of a broadband light source at the sample to be tested; or light emitted as fluorescence from a sample to be tested following excitation of the sample to be tested.

The spectroscopic intensity and wavelength of a spectroscopic substance may be measured by any methods for spectroscopic analysis known and appreciated by one or ordinary skill in the art. Spectroscopic methods that may be utilized in the present invention include, but are not limited to, a laser and photodetector pair system or more complex optics known to those of skill in the art where the path of an optical beam intersects with the path of a spectroscopic substance and the excitation or illumination of the spectroscopic substance is captured by an optical path comprising one or more objective, mirror, and/or lens to direct the light to a photomultiplier tube (PMT) or photosensitive camera. A known fluoroscopy method that will be known and appreciated by one of skill in the art for use in the present invention is the use of flow cytometry instrumentation.

The spectroscopic intensity measurements may comprise one or more methods, including but not limited to, light scatter, absorption, chemiluminescence, fluorescent intensity, radiation decay counts, colorimetric, and so forth.

Samples to be tested are placed in the path of an excitation energy source such as a light source selected from but is not limited to, lasers, light-emitting diodes (LEDs), arc lamps, broadband light source, and high intensity light bulbs. The spectroscopic substances in the sample to be tested scatter, absorb, chemiluminesce, or fluoresce (also referred to herein as "signal") in the form of light at a wavelength substantially different from the wavelength of the light source. This light from the sample to be tested is then captured by a detector or sensor, which may be selected from but is not limited to, a camera, a charge coupled device (CCD), a complementary metal-oxide-semiconductor (CMOS) (alternatively referred to as a complementary-symmetry metal-oxide-semiconductor (COS-MOS)), one or more individual photodiodes, photodiode arrays (PDAs), avalanche photodiodes (APDs), avalanche photodiodes arrays, photomultiplier tubes (PMTs), or photomultiplier tube arrays.

Known optical or electronic means may be optionally used to amplify the light from the light source and/or the light from the sample to be tested and/or to separate one or both into its component wavelengths. Selecting a reference spectroscopic substance and one or more sample spectroscopic substances for a particular sample to be tested such that each spectroscopic substance scatters light, selectively absorbs light, emits light in the form of chemiluminescence or fluorescence, depending upon the spectroscopic substance and particular application, at substantially different wavelengths allowing for easier separation of the respective wavelengths. The difference between the reference spectroscopic substance's expected value and measured value can be used to quantify the contribution of "noise" to the output, assuming the reference spectroscopic substance and the one or more sample spectroscopic substances are subject to the same measurement conditions (e.g., the power of the light source, detector or sensor noise, humidity, heat, pH of the sample to be tested, and the vehicle that the sample to be tested itself is in). The contribution of "noise" to the reference spectroscopic substance signal should correlate with the contribution of noise to the signal of the one or more sample spectroscopic substances. This correlation may be, and is typically, proportional but could vary linearly, exponentially, or in other manners or functions as well.

In one embodiment, the system of the present invention may be used to perform methods for detecting the presence or absence of a particular nucleic acid sequence, referred to herein as the "target nucleic acid", such as those methods described, for example, in WO 2012/078710, which is incorporated herein by reference in its entirety. The target nucleic acid is a nucleic acid sample obtained from a human, animal, plant or any other organism or microorganism, and includes, but is not limited to, genomic DNA, mitochondrial DNA, cDNA, and others. The target nucleic acid may be double stranded or single stranded. In one embodiment, a double stranded target nucleic acid is first converted to a single stranded target nucleic acid. The target nucleic acid may be double stranded or single stranded. In one example, the single stranded target nucleic acid is DNA. In one embodiment, a double stranded target nucleic acid is first converted to a single stranded target nucleic acid. In yet another embodiment, PCR is performed on the target nucleic acid prior to detection. In one aspect of this embodiment, the PCR product is subsequently converted to single stranded form.

In one aspect of this embodiment, a single nucleotide within a sample is detected. In another aspect of this embodiment, a particular locus may be queried to detect the presence or absence of a particular nucleic acid sequence variance. A "variance" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variance" are used interchangeably herein. As used herein, the term "variance" in the singular is to be construed to include multiple variances, i.e., two or more nucleotide additions, deletions and/or substitutions in the same polynucleotide. A "point mutation" refers to a single substitution of one nucleotide for another.

For example, the sample may comprise a particular locus that may be queried to detect the presence or absence of a single nucleotide polymorphism. A "single nucleotide polymorphism" or "SNP" refers to a variation in the nucleotide sequence of a polynucleotide that differs from another polynucleotide by a single nucleotide difference. A SNP includes, for example and without limitation, exchanging one A for one C, G or T, or one C for one G, T or C and so on, in the entire sequence of polynucleotide. Additionally, it is possible to have more than one SNP in a particular nucleic acid sequence. For example, at one position in a nucleic acid sequence, a G may be exchanged for an A, at another position a C may be exchanged for a T and so on. In another example, the sample may comprise PCR product comprising the amplified product of a single nucleotide mutation.

In another example, a particular locus may be queried to detect the presence or absence of a single nucleotide mutation. In another embodiment, a plurality of nucleotide targets (e.g., two or more nucleotides) is detected within the same sample. In one aspect of this embodiment, a short nucleic acid sequence within the target nucleic acid sequence in detected. In one example, the nucleic acid probe is as short as about 6 to 8 nucleotides long. In another aspect of this embodiment, a full complement of short nucleic acid probes can be used sequentially to determine the entire sequence of the target nucleic acid. For example, the full complement of short nucleic acid probes may be a set of all 4096 possible hexamers. Accordingly, a target nucleic acid may be detected using the methods of this invention with no specific target length limitation.

In one embodiment of the present invention, a nucleic acid sample may be injected into the system by the user. The system then injects this sample into a multitude of droplets, present within an emulsion, containing the reagents necessary for a polymerase chain reaction (PCR) amplification reaction, with the droplets being referred to as "PCR droplets." Next the PCR droplets are thermally cycled for PCR amplification after which each of the PCR droplets is injected into a multitude of probe droplets. PCR using water-in-oil emulsions may be done using standard PCR conditions, as will be known and understood by one of skill in the art and described, for example, by Williams, et al., "Amplification of Complex Gene Libraries by Emulsion PCR", *Nature Methods* (2006), vol. 7, pp. 545-50; Diehl, et al., "BEAMing: Single-Molecule PCR on Microparticles in Water-in-Oil Emulsions", *Nature Methods* (2006), vol. 7, pp. 551-59; and Porreca, et al., "Polony DNA Sequencing", In: F. Ausubel, ed. 2006. *Curr Protoc Mol Biol.*, Chapter 7, Unit 7.8. For example, the probe droplets may contain nucleic acid probes and the chemical reagents necessary for a probe-hybridization assay. In this example, the assay may result in fluorescent signal only if the probes hybridize to the injected sample, as described in WO 2012/078710. The data acquired is processed and analyzed by the system of the present invention. Accordingly, data from multiple probe droplets may be used for DNA sequencing of a nucleic acid sample, as described herein and in WO 2012/078710.

Figure 3:
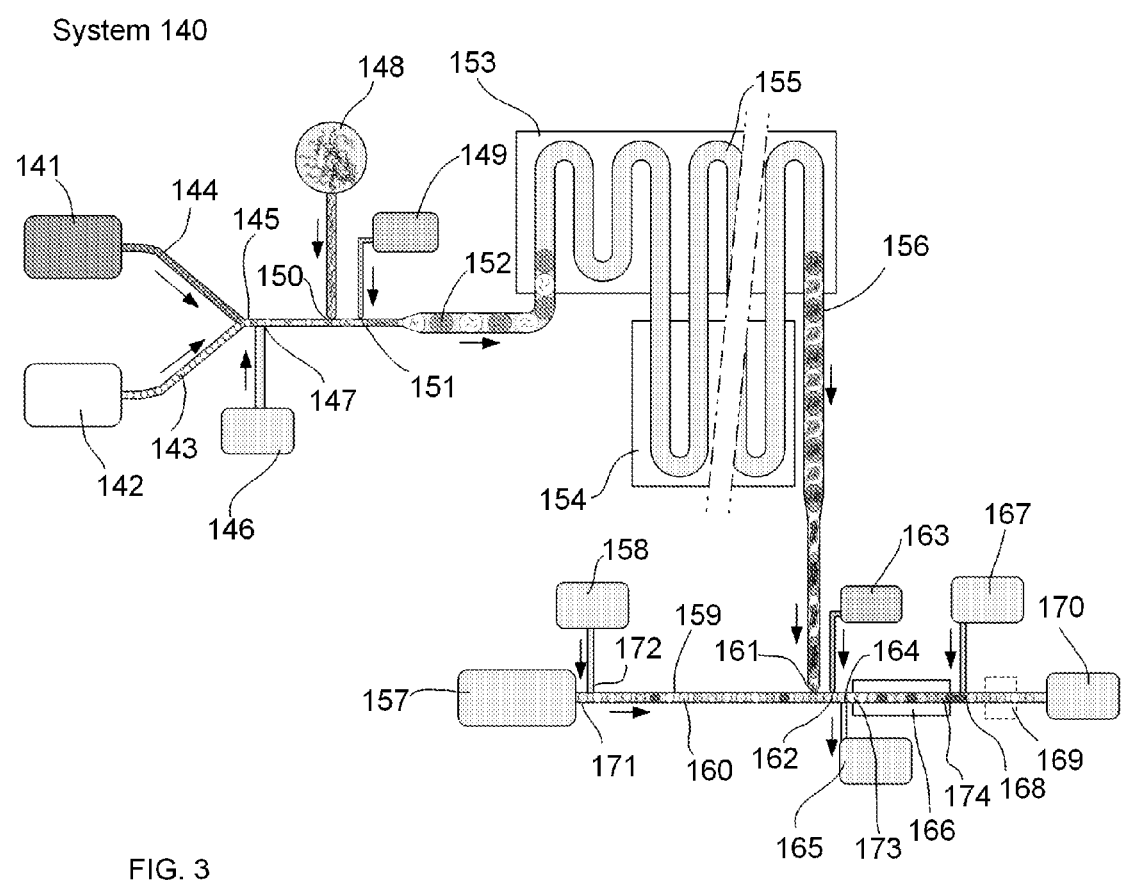
FIG. 3 is an illustration of an example of one embodiment of the system, according to the present invention, performing a cascading assay.

FIG. 3 is an illustration of an example of one embodiment of the system according to the present invention for performing a cascading assay. In this example, a two-stage integrated emulsion-based microfluidic system 140 is illustrated, wherein the system may be used to perform a cascading assay comprising a first stage and a second stage, as discussed in greater detail below. The system 140 in this example provides for the performance of various functions, including but not limited to, target nucleic acid selection and amplification, assay, detection and data analysis. However, the system, samples and reagents may be modified accordingly to perform any type of assay, as described herein.

In the first stage of the cascading assay performed by the system 140, sample DNA is introduced into a sample vessel 148. PCR primers that are uniquely labeled (e.g., with unique fluorophores) and contained within droplets (primer droplets) in the form of an emulsion are introduced into reagent vessels 141 and 142. The primer droplets in reagent vessel 141 flow in primer channel 144 and primer droplets in reagent vessel 142 flow in primer channel 143. Primer channel 143 intersects with primer channel 144 at microfluidic channel 145. The primer droplets flow in primer channels 143 and 144 in a manner such that the primer droplets enter microfluidic channel 145 in an alternating manner. DNA polymerase is introduced into reagent vessel 149. Sample vessel 148 and reagent vessel 149 each further comprise selection and amplification reagents and components such as, but not limited to, PCR primers, buffers, dNTPs, and BSA (bovine serum albumin).

In this example, primer droplets in reagent vessel 141 are labeled differently than those in reagent vessel 142 such that the labels may be monitored at a final detection stage. Upon entering microfluidic channel 145, the primer droplets are spaced relatively uniformly with oil comprising a surfactant from oil vessel 146 (or, alternatively, any fluid capable of maintaining droplet separation). This results in relatively uniformly spaced primer droplets 147, wherein the primer droplets 147 are spaced at a relatively uniform distance at a particular flow rate. Each of the uniformly spaced primer droplets 147 is first injected with sample from sample vessel 148 by way of the sample vessel injector 150, followed by injection with DNA polymerase from reagent vessel 149 by way of the reagent injector 151. In an alternative embodiment of the example illustrated in FIG. 3, the order of injection may be reversed such that the DNA polymerase is injected first followed by injection of sample into each primer droplet 147. In this example, electrodes (not shown) provide a mechanism for disrupting the interface between the primer droplets 147 and a fluid and/or emulsion comprising the material (sample and DNA polymerase, in this example) being injected into the primer droplets 147.

This process results in the formation of relatively larger droplets 152, wherein each droplet comprises sample DNA, primers and PCR reagents, flowing within the microfluidic channel 145. The droplets 152 next flow through a serpentine-like microfluidic channel 155 while repeatedly passing through two temperature zones, first temperature zone 153 and second temperature zone 154, respectively, as part of the process of undergoing PCR amplification of the sample DNA. First temperature zone (denaturation temperature zone) 153 allows for the denaturing of the sample DNA, whereas second temperature zone (elongation temperature zone) 154 allows for the elongation of sample DNA. Alternatively, the system may be modified to allow for a three-step PCR process whereby the sample DNA is PCR amplified by being subjected to multiple controlled temperature zones within the system, as will be understood and appreciated by one of skill in the art. As the droplets 152 flow through the serpentine-like microfluidic channel 155, they pass through alternating temperature zones 153 and 154 as part of the PCR process resulting in PCR product droplets 156 comprising PCR-amplified sample DNA.

The system 140 further comprises a DNA probe droplet vessel 157 comprising a library of DNA probes contained within droplets. Droplets comprising DNA probes (probe droplets) 160 are injected from DNA probe droplet vessel 157 by way of DNA probe droplet injector 171, which intersects with microfluidic channel 159. As the probe droplets 160 are injected into microfluidic channel 159, they are relatively uniformly spaced by oil injected from oil vessel 158 by way of oil injector 172.

In the second stage of the cascading assay performed by the system 140, as the PCR product droplets 156 flow through the serpentine-like microfluidic channel 155, a portion or all of each individual PCR product droplet 156 may be injected into one or more probe droplets 160 flowing in microfluidic channel 159 by way of injector 161 at the point at which the serpentine-like microfluidic channel 155 intersects with microfluidic channel 159. Next, the probe droplets 160 are injected with detection assay reagents (e.g., reagents for a sequencing reaction) from reagent vessel 163 by way of reagent vessel injector 162. Alternatively, the system 140 in this example may be modified such that the order of injection may be reversed, i.e., the detection assay reagents are injected into the probe droplets 160 prior to injection of PCR product droplets 156. In this example, electrodes (not shown) provide a mechanism for disrupting the interface between the probe droplets 160 and a fluid and/or emulsion comprising the material (PCR product droplets and detection assay reagents, in this example) being injected into the probe droplets 160. Despite the order of injection, the result is droplets comprising probe plus amplified sample, referred to herein as pre-incubation droplets 173.

Excess oil may be removed from microfluidic channel 159 by an oil remover 164 and collected in waste vessel 165. Removing excess oil allows for tight packing as the pre-incubation droplets 173 next pass through incubation temperature zone 166 while flowing in a relatively uniform manner allowing for each droplet to undergo relatively the same amount of incubation time and to remain a member of a collective unit of pre-incubation droplets 173 as opposed to receiving a variable incubation time or straying from the other pre-incubation droplets. The temperature of incubation temperature zone 166 may comprise one, two or multiple temperatures; one, two or multiple temperature gradients; one, two or multiple temperature cycles, or any combination of the above. Following incubation, the droplets are referred to as post-incubation droplets 174, which then pass through the temperature zone 166 in a relatively uniform manner by being spaced with oil from oil vessel 167 via oil injector 168. The relatively uniform spacing of the probe droplets 160 must be sufficient to separate the post-incubation droplets 174 for individual detection and analysis by the detector 169 and the user. After detection, the post-incubation droplets 174 are collected in a waste well 170.

Figure 4:
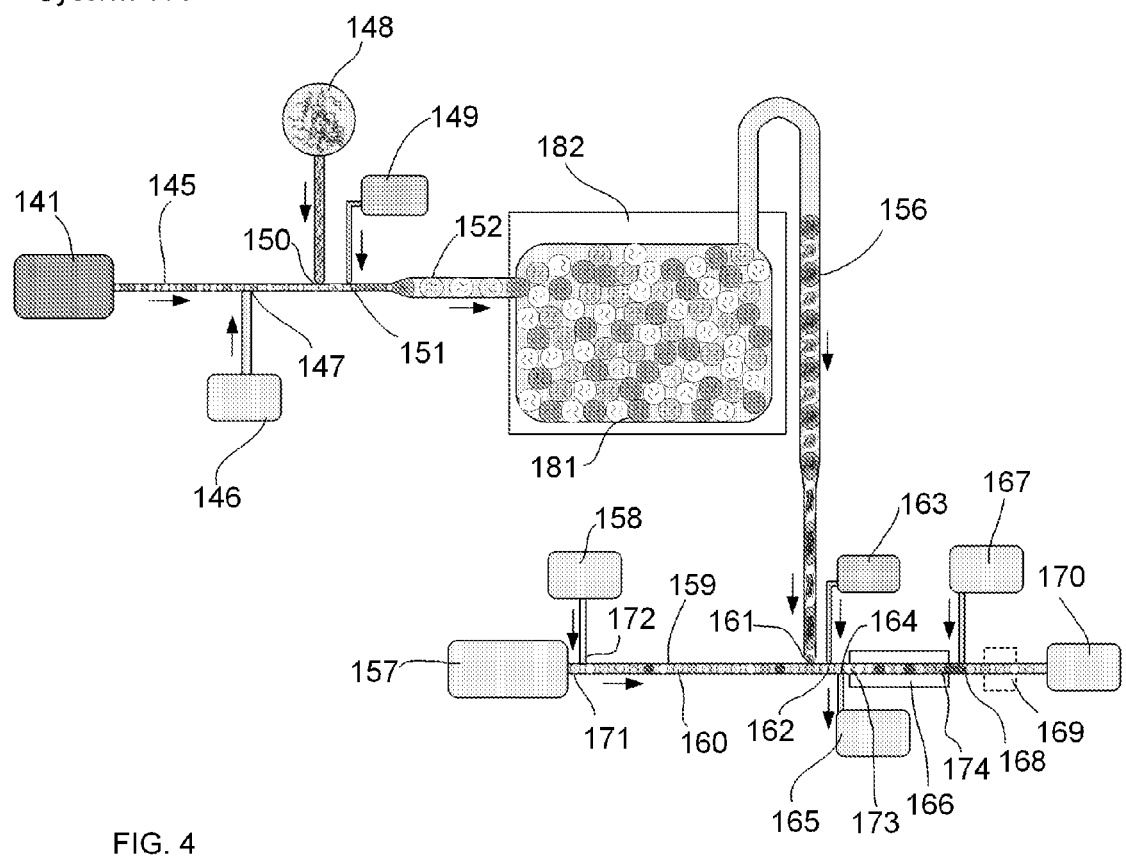
FIG. 4 is an illustration of an example of another embodiment of the system, according to the present invention, performing a cascading assay.

FIG. 4 is an illustration of an example of another embodiment of the system according to the present invention for performing a cascading assay. In this example, a two-stage integrated emulsion-based microfluidic system 180 is illustrated, wherein the system may be used to perform a cascading assay comprising a first stage and a second stage, similar to that previously described in FIG. 3 with a few modifications. Unlike the design of system 140 in FIG. 3, the droplets in this system 180 are introduced from a single well 141 with a random mix of different labels (for example, spectroscopic labels including but not limited to, fluorescent dyes) and, optionally, varied concentrations thereof, to differentiate the droplets and/or samples at the time(s) of detection. Additionally, the system 180 uses a static reaction chamber 181 as opposed to the constant flow serpentine-like microfluidic channel 155 of system 140 in FIG. 3. The droplets 152 are collected into the static reaction chamber 181 where they undergo thermocycling for a PCR reaction in a single controlled temperature zone 182. After a period of incubation, the resulting PCR product droplets 156 comprising PCR-amplified sample DNA flow out of the static reaction chamber 181 for the continuation of the cascading assay in relatively the same manner as in system 140 of FIG. 3.

Figure 5:
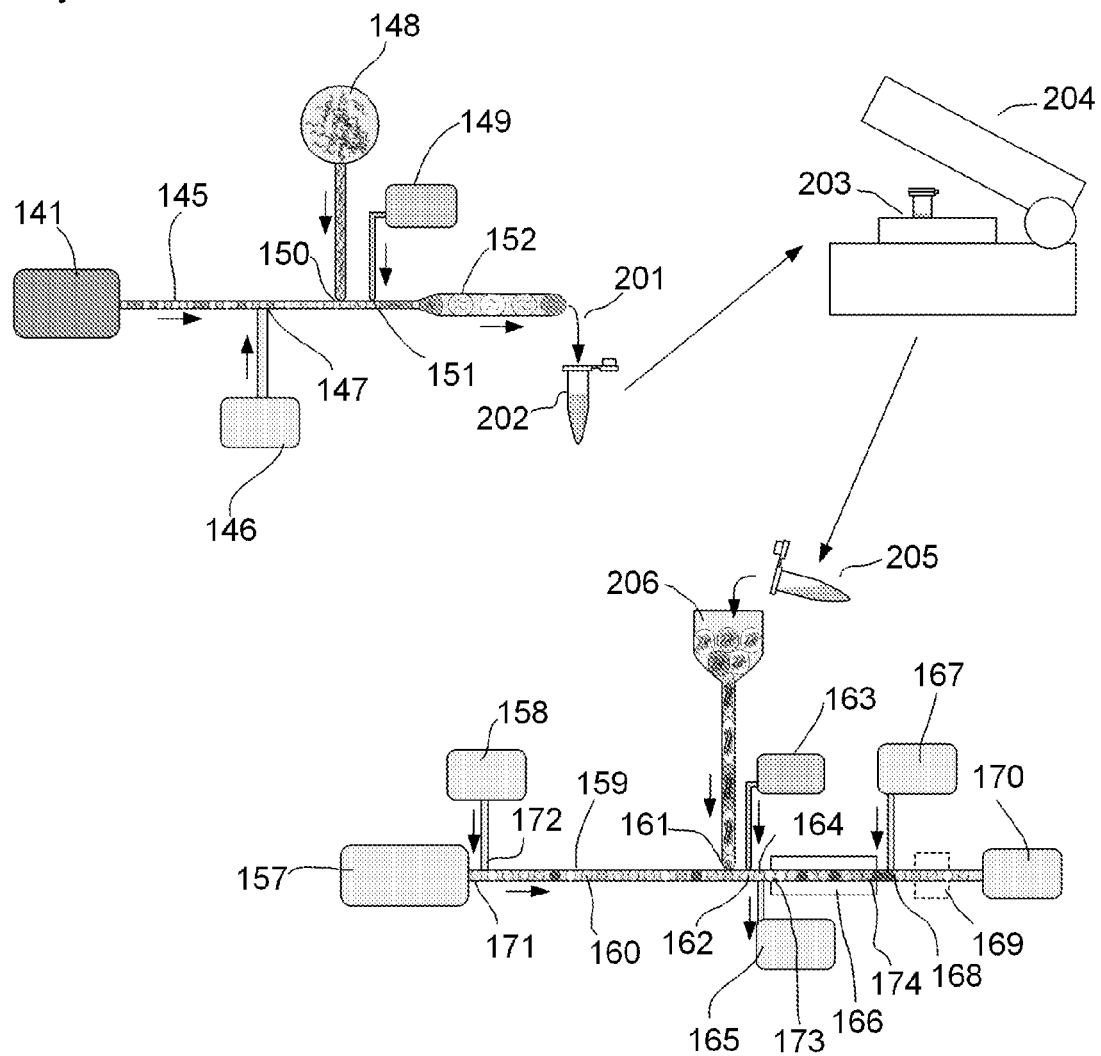
FIG. 5 is an illustration of an example of another embodiment of the system, according to the present invention, performing a cascading assay.

FIG. 5 is an illustration of an example of another embodiment of the system according to the present invention for performing a cascading assay. In this example, a two-stage integrated emulsion-based microfluidic system 200 is illustrated, where the system 200 is similar to that illustrated in FIG. 3 with the exception that the droplets 152 are manually, semi manually or fully automatically collected 201 into a separate vesicle 202, and then placed 203 into a processing system 204 (which may be offline, integrated, or inline), wherein the processing system 204 may be, for example but not limited to, a thermo-cycler, centrifuge or other process instrumentation and/or tools known and appreciated by one of skill in the art. This modification of the system according to the present invention, as illustrated by way of example in system 200, allows for the user to easily modify the cascading assay to change parameters, conditions and/or steps. After completion of the first assay stage, the resulting material 205 is transferred into a cascading workflow 206 for continuation of the cascading assay. In other embodiments of the system according to the present invention, a separate vesicle 202 may be utilized at any stage of a cascading assay to provide for modifications to the assay as described above, according to the preference of the user, as will be appreciated by one of skill in the art. For example, one of skill in the art will appreciate that incubation temperature zone 166 may be employed offline, yielding flexibility.

The present invention also pertains to methods for performing an assay comprising the system as previously described. The present invention also pertains to a kit containing the system and reagents necessary for performing cascading assays according to the present invention, as described previously. The present invention further incorporates the methods and apparatus necessary to transform any set of assay signals or readout into a coherent representation of a sample or any molecule isolated from a sample. This representation may take an electronic form and may include a digital readout. For example, the readout may comprise information related to the sequence of a nucleotide or peptide molecule along with any differences as compared to some reference target.

The results of the system, methods and kits of this invention, referred to herein as "data", then be kept in an accessible database, and may or may not be associated with other data from that particular sample or with data from other samples. Data obtained may be stored in a database that can be integrated or associated with and/or cross-matched to other databases.

The methods and kits of this invention may further be associated with a network interface. The term "network interface" is defined herein to include any person or computer system capable of accessing data, depositing data, combining data, analyzing data, searching data, transmitting data or storing data. The term is broadly defined to be a person analyzing the data, the electronic hardware and software systems used in the analysis, the databases storing the data analysis, and any storage media capable of storing the data. Non-limiting examples of network interfaces include people, automated laboratory equipment, computers and computer networks, data storage devices such as, but not limited to, disks, hard drives or memory chips.

Although the present invention and its advantages have been described in detail, it should be understood that various changes, substitutions and alterations can be made herein without departing from the spirit and scope of the invention as defined in the appended claims.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for forming assay droplets comprising the steps of:
   providing a microfluidic device comprising a first plurality of reagent droplets, the first plurality of reagent droplets comprising a first reagent set, and a second plurality of reagent droplets, the second plurality of droplets comprising a second reagent set;
   forming, from a sample and the first plurality of reagent droplets, a first plurality of assay droplets in the microfluidic device, wherein the forming comprises injecting in the microfluidic device at least a portion of a sample into some or all of the first plurality of reagent droplets; and
   forming, from the first plurality of assay droplets and the second plurality of reagent droplets, a second plurality of assay droplets, wherein the forming comprises injecting in the microfluidic device different portions of an assay droplet from the first plurality of assay droplets into multiple droplets from the second plurality of reagent droplets, thereby creating a second plurality of assay droplets in the microfluidic device.

2. The method of claim 1, further comprising detecting the product of a chemical reaction in the second plurality of assay droplets.

3. The method of claim 1, further comprising injecting a reagent into the first plurality of reagent droplets or the first plurality of assay droplets.

4. The method of claim 3, wherein the reagent is a polymerase.

5. The method of claim 4, further comprising thermocycling the first plurality of assay droplets.

6. The method of claim 2, wherein the detecting occurs within the microfluidic device.

7. The method of claim 3, wherein the first plurality of reagent droplets comprises a primer library.

8. The method of claim 7, wherein the first plurality of reagent droplets comprise labels.

9. The method of claim 7, wherein the reagent is a DNA polymerase.

10. The method of claim 9, wherein the second reagent set comprises a library of nucleic acid probes.

11. The method of claim 10, wherein the nucleic acid probes are random hexamers.

12. The method of claim 10, wherein the detecting comprises detecting the hybridization of one or more of the nucleic acid probes to a product of a chemical reaction in the second plurality of assay droplets.

13. The method of claim 1, further comprising conducting a first chemical reaction in the first plurality of assay droplets.

14. The method of claim 13, wherein the first chemical reaction is conducted in the microfluidic device.

15. The method of claim 14, further comprising conducting a second chemical reaction in the second plurality of assay droplets.

16. The method of claim 15, wherein the first chemical reaction is conducted in the microfluidic device.

17. The method of claim 1, wherein one or more of (a) the first plurality of reagent droplets, (b) the first plurality of assay droplets, (c) the second plurality of reagent droplets, or (d) the second plurality of assay droplets are the aqueous phase of an emulsion.

18. The method of claim 15, wherein the second chemical reaction comprises contacting one or more probe to an amplified nucleic acid in the assay droplets.

19. The method of claim 18, wherein the one or more probe is 6-8 nucleotides long.

20. The method of claim 18, wherein the one or more probe queries a locus to detect the presence or absence of a particular nucleic acid sequence variance.

21. The method of claim 18, wherein hybridization of the probes determines the sequence of the nucleic acid.

* * * * *